United States Patent [19]

Hostetler et al.

[11] Patent Number: 5,194,654

[45] Date of Patent: Mar. 16, 1993

[54] LIPID DERIVATIVES OF PHOSPHONOACIDS FOR LIPOSOMAL INCORPORATION AND METHOD OF USE

[75] Inventors: Karl Y. Hostetler, Del Mar; Raj Kumar, San Diego, both of Calif.

[73] Assignee: Vical, Inc., San Diego, Calif.

[21] Appl. No.: 440,898

[22] Filed: Nov. 22, 1989

[51] Int. Cl.$^5$ .............................................. C07F 9/40
[52] U.S. Cl. ................................... 558/152; 558/169; 558/170; 558/180; 558/181; 558/182
[58] Field of Search ............... 558/169, 180, 181, 152, 558/170

[56] References Cited

U.S. PATENT DOCUMENTS 4,215,113  7/1980  Eriksson et al. ..................... 514/120
4,771,041  9/1988  Ericksson et al. ................... 514/120

FOREIGN PATENT DOCUMENTS 0300687  7/1988  European Pat. Off. .

OTHER PUBLICATIONS

E. Helgestrand et al., (1978) *Science* (Washington, D.C.) 201: 819.
M. S. Fischl et al., (1987) *New Eng. J. Med.*, 317: 185–191.
D. D. Richman et al., (1987) *New Eng. J. Med.*, 317: 192–197.
D. D. Richman et al., (1987) *J. Exp. Med.*, 166: 1144–1149.
R. Lambert et al., (1989) *J. Med. Chem.*, 32: 367–374.
T. Matsushita et al., (1981) *Cancer Res.*, 41: 2707–2713.
D. H. W. Ho and G. L. Neil, (1977) *Cancer Res.*, 37: 1640–1643.

(List continued on next page.)

Primary Examiner—Mary C. Lee
Assistant Examiner—Michael G. Ambrose
Attorney, Agent, or Firm—Knobbe, Martens, Olson & Bear

[57] ABSTRACT

Compounds are disclosed for treating viral infections due to herpes, influenza, hepatitis B, Epstein-Barr, and varicella zoster viruses, as well as cytomegalovirus and human immunodeficiency virus (HIV) by means of lipid derivatives of antiviral agents. The compounds consist of lipid derivatives of phosphonoacids having antiviral activity which are linked, commonly through the phosphate group of the phosphonoacid, to one of a selected group of lipids.

The lipophilic nature of these compounds provides advantages over the use of the phosphonoacids alone. It also makes it possible to incorporate them into the lamellar structure of liposomes when combined with similar molecules. In the form of liposomes, these antiviral molecules are preferentially taken up by macrophages and monocytes, cells which have been found to harbor the target human immunodeficiency virus (HIV). Additional site specificity may be incorporated into the liposomes with the addition of ligands, such as monoclonal antibodies or other peptides or proteins which bind to viral proteins.

Effective phosphonoacids are phosphonoformic acid or phosphonoacetic acid; lipid groups may be glycolipids, sphingolipids, phospholipids, glycerolipids, or fatty acids. The compounds persist, after intracellular hydrolysis, as the antiviral phosphonoacids. The compounds are effective in improving the efficacy of antiviral phosphonoacids by prolonging the antiviral activity after the administration of the drug has ended, and in preventing retroviral replication in HIV infections which have become resistant to therapy with conventional forms of the antiretroviral agents.

13 Claims, 1 Drawing Sheet

OTHER PUBLICATIONS

A. D. Bangham et al., (1965) *J. Mol. Biol.*, 13: 238–252.
C. D. V. Black et al., (1977) *Trans. Roy. Soc. Trop. Med. Hyg.*, 71: 550–552.
C. R. Alving et al., (1978) *Proc. Natl. Acad. Sci. USA*, 75: 2959–2963.
G. Lopez-Berestein, (1986) *Ann. Int. Med.*, 105: 130–131.
E. H. Herman et al., *Cancer Res.*, 43: 5427–5431.
M. Ostro, (1987) *Sci. Am.*, 256: 103–111.
B. Oberto, (1983) *Pharmacol. Ther.*, 19: 387–415.
F. C. Szoka, Jr. and C. J. Chu, (1988) *Antimicrobial Agents and Chemotherapy*, 32 (6): 858–864.
S. Z. Salahuddin et al., (1986) *Blood*, 68: 281–284.
S. Koenig et al., (1986) *Science*, 233: 1089–1093.
G. Poste et al., (1984) *Liposome Technology*, vol. III, G. Gregoriadis, ed., CRC Press Boca Raton, pp. 1≧28.
G. Scherphof, (2986) *Lipids and Biomembranes, Past, Present and Future*, J. A. F. Op den Kamp et al., Eds., Elsevier North Holland, Amsterdam, pp. 113–136.
B. W. Agranoff and W. D. Suomi, (1963) *Biochemical Preparations*, 10: 47–51.
F. Olson et al., (1979) *Biochim. Biophys. Acta*, 577: 9–23.
F. Szoka, Jr. et al., (1978) *Proc. Nat. Acad. Sci. USA*, 75: 4194–4198.
E. Mayhew et al., (1984) *Biochim. Biophys. Acta*, 775: 169–174.
S. Kin et al., (1983) *Biochim. Biophys. Acta*, 728: 339–348.
L. D. Mayer et al., (1986) *Biochim. Biophys. Acta*, 858: 161–168.
A. F. Rosenthal and R. P. Geyer, (1960) *J. Biol. Chem.*, 235 (8): 2202–2206.
L. D. Leserman et al., (1980) *Nature*, 288: 602–604.
B. A. Larder et al., (1989) *Science*, 243: 1731–1734.
E. G. Bligh and W. J. Dyer, (1959) *Can. J. Biochem. & Physiol.*, 37: 911–917.

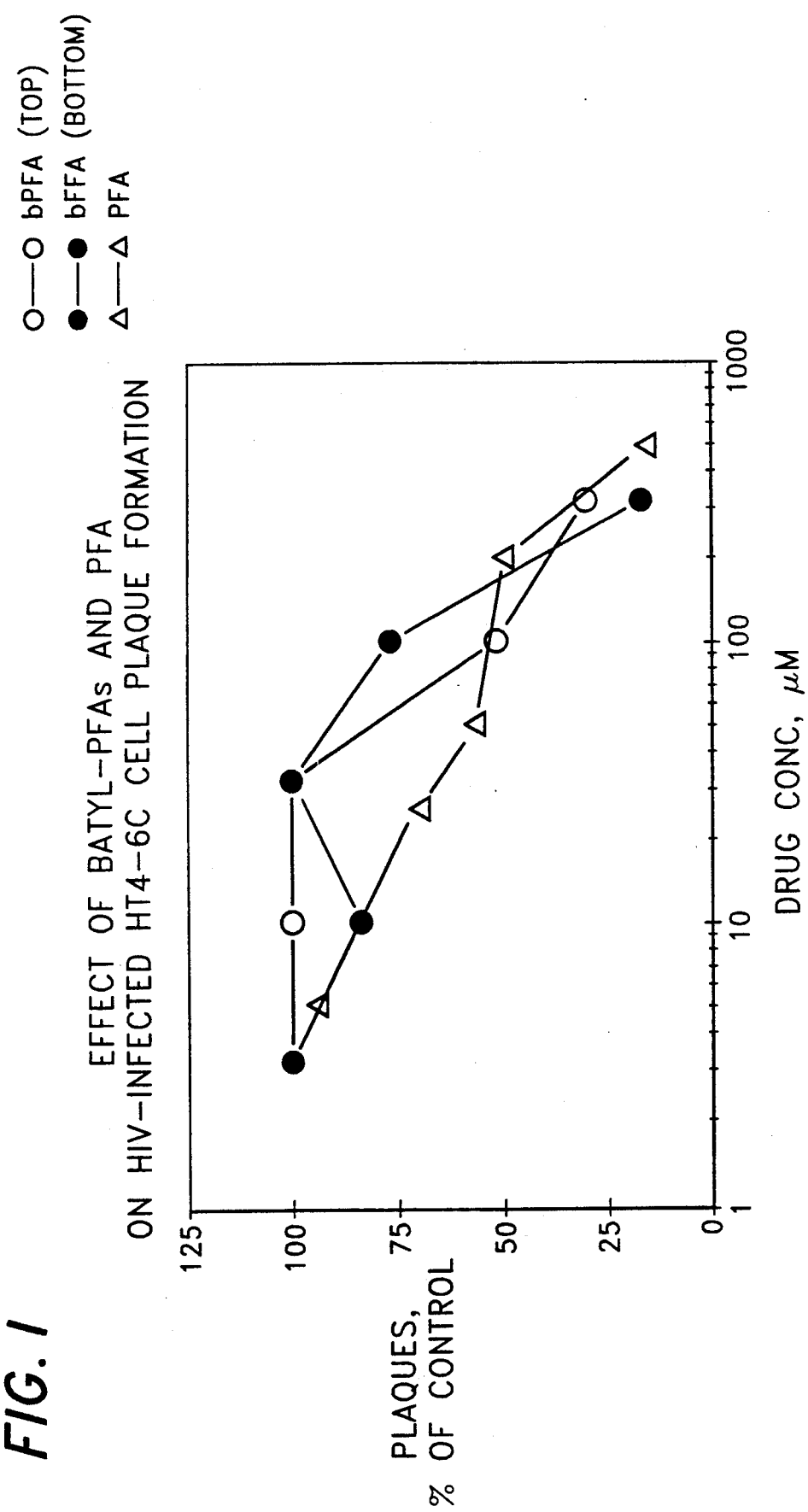

LIPID DERIVATIVES OF PHOSPHONOACIDS FOR LIPOSOMAL INCORPORATION AND METHOD OF USE

BACKGROUND OF THE INVENTION

The present invention relates generally to the treatment of viral infections using lipid derivatives of antiviral compounds. The lipid derived compounds can be integrated into the structure of liposomes, thereby forming a more stable liposomal complex which can deliver greater amounts of these compounds to target cells with less toxicity. More particularly, the present invention relates to lipid derivatives of antiviral phosphonoacids and their use.

The publications and other reference materials referred to herein are hereby incorporated by reference, and are listed for convenience in the bibliography appended at the end of this specification.

There has been a great deal of interest in recent years in developing agents to treat viral infections. In the past the most significant viral diseases were those caused by viruses of the herpes and influenza groups of viruses as well as those viruses causing hepatitis. In the past decade, infections with human immunodeficiency retrovirus (HIV) have become a major public health problem. Effective antiviral agents are those that interfere with the replication or transcription of viral genetic information while not inhibiting the normal functions of the host cell.

Phosphonoacetic acid (PAA) and phosphonoformic acid (PFA or Foscarnet), having the following structures:

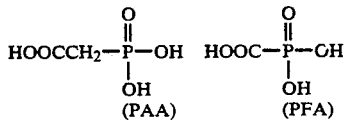

have been shown to have good antiviral activity against herpes simplex viruses types 1 and 2 (1), as well as against influenza viruses, hepatitis virus B, and retrovirus infections (2).

Acquired immunodeficiency syndrome (AIDS) is caused by the human immunodeficiency virus (HIV). HIV is a retrovirus which infects cells bearing the CD4 (T4) surface antigen, such as CD4+ helper lymphocytes, CD4+ monocytes and macrophages and certain other CD4+ cell types. The HIV infection of CD4+ lymphocytes results in cytolysis and cell death which contributes to the immunodeficiency of AIDS; however, CD4+ monocytes and macrophages may not be greatly harmed by the virus. Viral replication in these cells appears to be more prolonged and less cytotoxic than in lymphocytes, and as a result, monocytes and macrophages represent important reservoirs of HIV infection. It has recently been discovered that macrophages may serve as reservoirs of HIV infection even in certain AIDS patients who test negative for the presence of HIV antibodies. No effective cure is available for AIDS, although nucleoside analogues, particularly the dideoxynucleosides have been shown to prolong life and to reduce the incidence of certain fatal infections associated with AIDS.

Dideoxynucleoside analogues are the most potent agents currently known for treating AIDS, but these therapies are not entirely satisfactory. In a recent human clinical trial using AZT, serious toxicity was noted, evidenced by anemia (24%) and granulocytopenia (16%) (3,4). Certain monocyte-derived macrophages, when infected with some strains of HIV, have been found to be resistant to treatment with dideoxycytidine, azidothymidine, and other dideoxynucleosides in vitro as shown by Richman, et al. (5). The resistance may be due in part to the low levels of dideoxynucleoside kinase which result in a reduced ability to phosphorylate AZT, ddC or ddA.

Phosphonoformate (PFA) may provide an effective alternative therapy to nucleoside analogues. PFA inhibits a broad range of DNA polymerases as well as the RNA polymerase of influenza virus. PFA also inhibits the reverse transcriptase (RT) of HIV and other retroviruses at concentrations below 1 μM. Since the DNA polymerases are much less sensitive to PFA than the reverse transcriptases, the possibility exists that this drug may have a good therapeutic ratio for use in HIV infection. The phosphonoacids PFA and PAA may also supplement therapy using antiviral nucleosides. Lambert (6) has found that when PFA or PAA are coupled with certain antiviral nucleosides, particularly 5-bromo-2'-deoxyuridine (BUdR), the antiviral activity of the coupled nucleoside against herpes simplex viruses is greater than that of the parent nucleoside.

Efforts to increase the effectiveness of both antiviral nucleosides analogs and the phosphonoacids include association of these agents with lipids.

Attempts have been made to improve the therapeutic effectiveness of nucleoside analogues, such as arabinofuranosylcytosine (ara-C) and arabinofuranosyladenine (ara-A) as chemotherapeutic agents in the treatment of various types of cancer, by chemically linking them to phospholipids in order to enhance their catabolic stability (7). These phospholipid-derived agents showed a decreased toxicity and increased stability over the nucleoside analogues alone. However, they also exhibited poor cellular uptake (6) and poor drug absorption (8).

Another approach to increase the effectiveness of antiviral agents comprises encapsulation within liposomes to facilitate their delivery to cells. Liposomes are lipid vesicles which can be formed according to the method of Alex Bangham. Bangham and coworkers discovered in 1965 that dried films of phosphatidylcholine spontaneously formed closed bimolecular leaflet vesicles upon hydration (9). One of the most effective applications of liposomes in medicine is as a carrier to deliver therapeutic agents to target organs. The agents are encapsulated during the process of liposome formation and released in vivo after liposomes are taken up by cells. Liposomes thereby provide a means of delivering higher concentrations of therapeutic agents to target organs. Further, since liposomal delivery focuses therapy at the site of liposome uptake, it reduces toxic side effects.

Liposomal incorporation has been shown to provide a more effective way of delivering antiparasitic compounds which not only increases the potency of the dose but prolongs its efficacy and decreases its toxicity. For example, liposomal antimonial drugs are several hundredfold more effective than the free drug in treating leishmaniasis as shown independently by Black and Watson (10) and Alving, et al. (11). Liposome-entrapped amphotericin B appears to be more effective than the free drug in treating immunosuppressed patients with systemic fungal disease (12). Other uses for liposome encapsulation include restriction of doxorubicin toxicity (13) and diminution of aminoglycoside toxicity (14).

PFA has been found to inhibit HIV-1 replication in several in vitro systems at concentrations which are attainable in patients. However, the low degree to which PFA enters cells causes much higher levels to be required than that found to be effective in cell free systems with HIV RT (15). Also, PFA has toxic side effects and is known to accumulate in bone because of its similarity to pyrophosphate. Phosphonoacetic acid (PAA), which has antiviral activity similar to that of PFA, appears to have an affinity for bone that may preclude its use in humans (6).

Attempts have been made to increase the intracellular antiviral efficacy of the phosphonoacids by encapsulating them into liposomes. Szoka, F. and Chu, C. (16) found that liposomal delivery enhanced the cellular uptake and viral inhibitory activity of both PFA and PAA. Liposomal encapsulation also decreased the cytopathic effect of PFA; however, the cytopathic effect of liposomal PAA as compared to the free drug appeared to be increased.

As previously mentioned, it is now thought that macrophages are an important reservoir of HIV infection (17, 18). Macrophages are also a primary site of liposome uptake (19, 20). Accordingly, it would be desirable to utilize liposomes to enhance the effectiveness of antiviral phosphonoacid and antiviral phosphonoacid esters of antiviral nucleosides in treating AIDS and other viral infections. Clearly, it would be useful to have more effective ways of delivering large amounts of effective antiviral phosphonoformate compounds to macrophages infected with HIV or other viruses and to other cells having viral infections.

Co-pending applications U.S. Ser. Nos. 216,412 and 319,485 (21, 22), both abandoned, disclose lipid derivatives of nucleoside analogues which are capable of being incorporated into the structure of liposomes so as to further improve therapy comprising lipsomal delivery of these agents.

In order to use phosphonoacid antivirals more effectively, it is desirable to synthesize lipid prodrugs of the agents. It is therefore an object of the invention to provide methods for producing phosphonoacid lipid derivatives which can be incorporated into stable liposomal form.

The methods disclosed here apply not only to the use of lipid derivatives of phosphonoacids in the treatment of AIDS and other retroviral diseases, but also to their use in the treatment of diseases caused by other viruses, such as influenza, herpes simplex virus (HSV), human herpes virus 6, cytomegalovirus (CMV), hepatitis B virus, Epstein-Barr virus (EBV), and varicella zoster virus (VZV).

BRIEF DESCRIPTION OF THE DRAWINGS

FIG. 1 demonstrates the effect of a composition of the present invention on plaque formation in HIV-infected cells.

SUMMARY OF THE INVENTION

The invention provides a composition having antiviral properties, comprising an antiviral phosphonoacid having a lipid moiety linked thereto. The composition may further comprise an antiviral nucleoside linked to the phosphonoacid. In a preferred embodiment, the phosphonoacid is phosphonoformic acid, and in another embodiment, the phosphonoacid is phosphonoacetic acid. In compositions comprising an antiviral nucleoside which is linked to the phosphonoacid, the antiviral nucleoside may comprise a dideoxyribose. In a particularly preferred embodiment, the nucleoside is 3'-azido-3'-deoxythymidine.

According to one embodiment of the invention, the lipid moiety attached to the phosphonoacid is a monoacylglyceride or a diacylglyceride having fatty acid groups which are the same or different; in other embodiments, the lipid moiety is a fatty acid, a phosphatidic acid, or a more complex lipid moiety, such as, for example, a ceramide, cardiolipin, or bis(diacylglycero)-phosphate.

In accordance with another aspect of the invention, the lipid moiety may comprise from 1 to 4 long chain aliphatic groups, each comprising from 2 to 24 carbon atoms, which may be unsaturated, containing from 1 to 6 double bonds. The aliphatic groups of glycerides may be attached to the constituent glycerol unit by ester, ether, or vinyl ether bonds. The aliphatic groups of lipids having more than one such group may be the same or different in structure.

Specific compositions are provided having the formula:

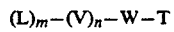

wherein
W is

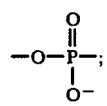

T is $(CH_2)_p$—C(O)—;
p=0 or 1;
V is phosphate;
n=0 to 2;
L is a lipid moiety;
m=1 to 3; and wherein each L is linked directly to V in a phosphoester linkage and T is linked to W through a phosphonate bond.

In another embodiment there are provided compositions having the formula:

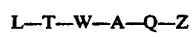

or

wherein
Z is the base portion of a nucleoside analogue;
Q is the pentose portion;
A is O, C, or S;
W is

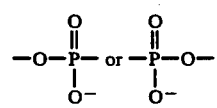

T is $(CH_2)_p$—C(O)—O—;

p=0 or 1; and

L is a lipid moiety linked directly to W or T through an ester bond and T is linked to W through a phosphonate bond.

In another embodiment, compositions are provided having the formula:

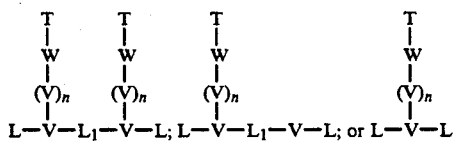

wherein
W is

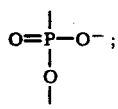

V is phosphate;
n=0 or 1;
T is $(CH_2)_p$—C(O)—O;
p is 0 or 1;
L is a lipid moiety;
$L_1$ is $(CH_2$—CHOH—$CH_2)$; and
wherein L and $L_1$ are each linked to V through a phosphoester bond and T is joined to W through a phosphonate bond.

In any of the above embodiments, L is independently selected from the group consisting of R;

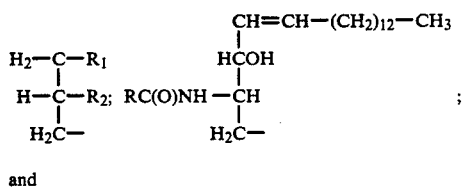

and

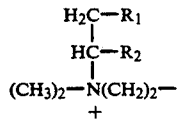

wherein R, $R_1$ and $R_2$ are independently $C_2$ to $C_{24}$ aliphatic groups in ester, ether, or vinyl ether linkage. In any of the specific compositions described, R, $R_1$ and $R_2$ independently have from 0 to 6 sites of unsaturation, and have the structure:

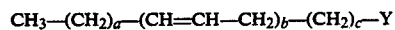

wherein the sum of a and c is from 0 to 22; and b is 0 to 6; and wherein Y is C(O)O—, C—O—, C=C—O—, C(O)S, C—S, or C=C—S.

The invention further comprises a liposome formed at least in part from any of the compositions of the invention.

The present invention also provides a method for synthesizing a glyceride derivative of a phosphonoacid, comprising the step of joining a monoglyceride, a diglyceride or batyl alcohol and a phosphonoacid with a coupling agent in the presence of a catalyst.

Still a further method provided by the invention is a method of synthesizing a glyceride derivative of a phosphonoacid-antiviral nucleoside conjugate, comprising joining a monoglyceride or a diglyceride and a phosphonoacid with a coupling agent in the presence of a catalyst to form a glycerophosphonoacid; converting said glycerophosphonoacid to an acyl chloride; and reacting said acyl chloride with an antiviral nucleoside whereby a nucleoside is linked to the glycerophosphonoacid. The derivative may be joined together in other suitable coupling reactions using, for example, in procedures using dicyclohexylcarbodiimide (DCCI).

Also a part of the present invention is a method for synthesizing a glyceride derivative of a phosphonoacid-antiviral nucleoside conjugate, comprising preparing the acyl chloride derivative of a phosphonoacid; forming a phosphonoacid glyceride by reacting the acyl chloride so formed with a monoglyceride or diglyceride; and joining the phosphonoacid glyceride and an antiviral nucleoside with a coupling reagent in the presence of a catalyst.

Also a part of the present invention is a method for preparing a suspension of liposomes for use in treating viral infections in a mammal, comprising providing an lipophilic antiviral agent selected from the group consisting of a phosphonoacid linked to a lipid moiety and a phosphonoacid linked at the same time to both a lipid moiety and a nucleoside analogue; combining the lipophilic antiviral agent and a pharmacologically acceptable aqueous solvent to form a mixture; and forming liposomes from the lipophilic antiviral agent.

The invention further comprises methods for treating viral infection in a mammal, comprising administering an effective amount of any one of the compositions of the invention. In a preferred embodiment, the mammal is a human, and the virus is the retrovirus HIV. In particularly preferred embodiments, a method of the invention is used in combination with the administration of AZT or other antiretroviral analogues. The methods may include avoiding or overcoming resistance to AZT or other antiviral analogues by administering the analogues in the form of one of the compositions of the invention.

DETAILED DESCRIPTION OF THE INVENTION

We have synthesized lipid derivatives of phosphonoacids which can be incorporated into the lipid bilayer of liposomes (Prosomes). These derivatives are converted into antiviral phosphonoacids by constituent metabolic processes, and they accordingly have antiviral effects in vivo and in vitro.

A phosphonoacid has the general structure

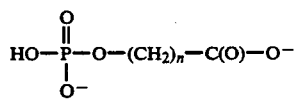

n is 0 to 1. In preferred embodiments of the invention, the phosphonoacid is phosphonoformic acid or phosphonoacetic acid.

Lipid Derivatives

Any lipid derivative of a phosphonoacid which possesses antiviral activity is within the scope of the invention. Compositions which will be most effective will have a lipid portion sufficient to be able to incorporate the material in a stable way into a liposomal bilayer, cell membrane, lipid bilayer, or other macromolecular array. Lipid groups attached to the phosphonoacids can be, for example, glycolipids, sphingolipids, phospholipids, glycerolipids, or fatty acids. Some preferred lipid derivatives of phosphonoacids fall into the following general classes:

1. Antiviral Phosphatidyl Phosphonoacids

The structure of a member of one class of these antiviral lipid compounds is shown below:

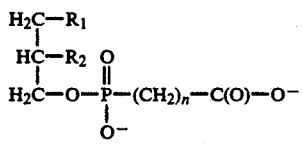

wherein n is 0 or 1; an aliphatic acid group, either formate or acetate, is joined to P through a phosphonate bond; and $R_1$ and $R_2$ are aliphatic groups, defined below.

This class of compounds may be prepared, for example, from the reaction of a diacylglycerol and phosphonoformic acid using triisopropylbenzenesulfonyl chloride in pyridine as described for the preparation of 1,2-dimyristoylglycero-3-phosphophonoformate in Example 1, or 1,2-dipalmitoyl-glycero-3-phosphophonoformate in Example 2.

2. 1-O-alkyl Glycerol Derivatives of Phosphonoacids

Other lipid derivative of antiviral phosphonacids are those synthesized by condensing phosphonoformates or phosphonoacetates with various analogs of 1-O-alkyl glycerol, wherein the analogs have an alkyl group of 2 to 24 carbon chain length at the 1-position of glycerol. The 1-O-alkyl group may consist of a saturated or unsaturated aliphatic group. The 1-O-alkyl glycerol may be racemic or stereospecific. These lipid derivatives have the general structure:

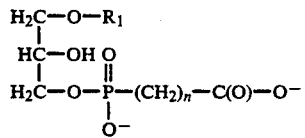

n is 0 or 1; an aliphatic acid group, either formate or acetate, is joined to P through a phosphonate bond; and $R_1$ and $R_2$ are aliphatic groups, defined below. Lipid derivatives of this type, comprising an aliphatic R group attached to a glycerol moiety through an ether link, may be prepared as indicated in Example 4.

3. Ceramide Antiviral Phosphonucleosides

Antiviral phosphonoacids can also be generated in cells after liposomal delivery of ceramide derivatives thereof having the general structure shown below:

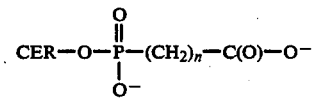

where n is 0 or 1 and CER is an N-acylsphingosine having the structure:

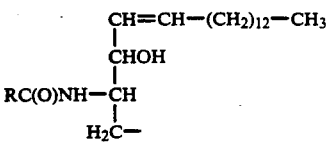

wherein R is an aliphatic group as defined below, or an equivalent lipid-substituted derivative of sphingosine. This class of compounds is useful in liposomal formulation in the therapy of AIDS and other viral diseases because it can be acted upon by sphingomyelinase or phosphodiesterases in cells giving rise to the antiviral phosphonoacid. In addition to the compound shown above, ceramide diphosphate phosphonoacids can also be synthesized, which may be degraded by cellular pyrophosphatases to give a phosphonoacid and ceramide phosphate.

Ceramide phosphonoacids may be prepared in a method similar to the method for preparing antiviral phosphonoacid diphosphate diglycerides, with appropriate changes to the starting materials.

4. Diacylglycerol Phosphate Phosphonoacids

The structure of a member of this class of antiviral phosphonoacid lipids is shown below:

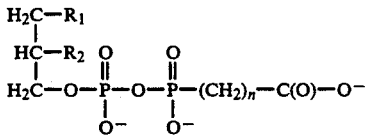

wherein n is 0 or 1; an aliphatic acid group, either formate or acetate, is joined to P through a phosphonate bond; and $R_1$ and $R_2$ are aliphatic groups, defined below.

This class of compounds may be synthesized by preparing the morpholidate derivative of the phosphonoacid and coupling to phosphatidic acid in dry pyridine as described for cytidine diphosphate diglyceride by Agranoff and Suomi (23). Alternatively, the morpholidate of phosphatidic acid may likewise be coupled to the phosphonoacid directly.

5. Lipid-Rich Derivatives of Antiviral Phosphonoacids

One approach to achieving even greater stability of lipid derivatives of phosphonoacids within liposomes is by increasing lipid-lipid interaction between the lipid-phosphonoacid structure and the lipid bilayer. Accordingly, in preferred embodiments, lipid derivatives of phosphonoacids having up to four lipophilic groups may be synthesized. One class of these comprises diphosphatidylglycerol derivatives, having the general structure:

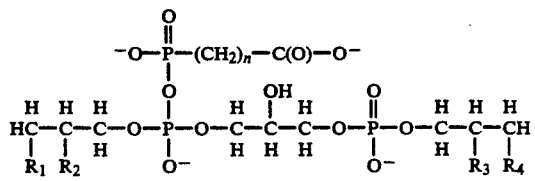

wherein n is 0 or 1, and $R_{1-4}$ are two, three or four aliphatic groups which are independently R as defined below, said groups being in acyl ester, ether, or vinyl ether linkages. In this class, phosphonoacids are attached to one or both phosphates by a diphosphate bond. There may be one or two phosphonoacids attached to each molecule.

Another class of phosphonoacid derivatives having increased lipid components comprises bis(diacylglycero)phosphate phosphonoacids, having the general structure:

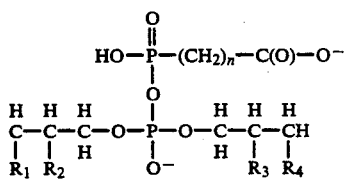

where n is 0 or 1, and $R_1$-$R_4$ are as defined previously.

This compound may be synthesized by joining a phosphono morpholidate to the phosphoester residue of bis(diacylglycero)phosphate. This compound will be metabolized to a phosphonoacid in the cells by endogenous pyrophosphatases or other esterases. These two types of compounds may provide superior metabolic and physical properties.

Other suitable lipid derivatives of phosphonoacids may be synthesized using novel lipids. It is desirable, for example, to synthesize phospholipid derivatives of antiviral and antiretroviral phosphonoacids which will give rise to potent antiviral agents upon alternate paths of metabolism by the target cells which take up the lipid formulation.

Substituent R groups $R_1$ and $R_2$, as well as $R_{3-4}$ for the bis(diacylglycero) species) may be the same or different, and are $C_2$ to $C_{24}$ aliphatic groups, having from 0 to 6 sites of unsaturation, and preferably having the structure

wherein the sum of a and c is from 0 to 22; and b is 0 to 40 and wherein Y is $C(O)O^-$, $C-O^-$, $C=C-O^-$, $C(O)S-$, $C-S-$, $C=C-S-$; forming acyl ester, ether or vinyl ether bonds, respectively, between the aliphatic groups and the glycerol moiety.

These aliphatic groups in acyl ester linkage therefore comprise naturally occurring saturated fatty acids, such as lauric, myristic, palmitic, stearic, arachidic and lignoceric, and the naturally occurring unsaturated fatty acids palmitoleic, oleic, linoleic, linolenic and arachidonic. Preferred embodiments comprise a monoester or diester, or a 1-ether, 2-acyl ester phosphatidyl derivative. In other embodiments, the aliphatic groups can be branched chains of the same carbon number, and comprise primary or secondary alkanol or alkoxy groups, cyclopropane groups, and internal ether linkages.

The glycero-phospho bonds may be racemic or sn-1 or sn-3 ester bonds; alternatively, the phosphate group may be joined at the 2-position of the glycerol moiety. There may be 1 or 2, (as well as 3, or 4 for the bis(diacylglycero) species) acyl ester groups, or alkyl ether or vinyl ether groups, as required.

Further Compounds for Combination Therapy

In addition to using pPFA in combination with phosphatidyl AZT and other liponucleotides incorporated into the same liposome, it is also possible to link AZT and other antiviral and antiretroviral nucleosides directly to pPFA or pPAA by carboxyl ester linkage to the 5'-hydroxyl (or equivalent) of the nucleoside as shown in Example I below:

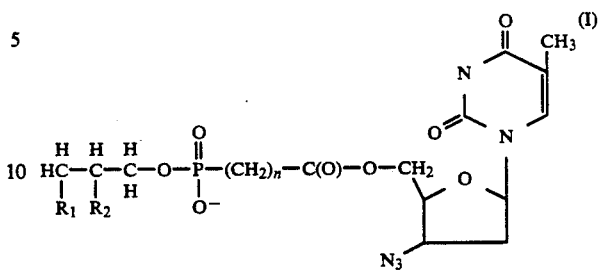

In addition, the PFA may be esterified to 1,2 diacylglycerol by a carboxyl ester linkage by preparing the acyl chloride of PFA and reacting it directly with diacylglycerol, 1-alkyl, 2-acyl glycerol, or batyl alcohol and its congeners. The structure of this conjugate is shown in Example II below:

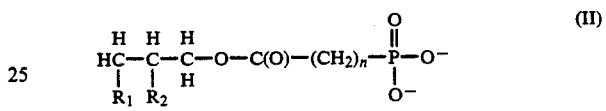

This class of compounds can also receive an antiretroviral or antiviral nucleoside on the phosphate by condensation using triisopropylbenzenesulfonyl chloride (TPS) or other coupling agents. Any antiviral nucleoside may be linked to the phosphate residue of the above compound. The structure of such a compound with AZT is shown in Example III below:

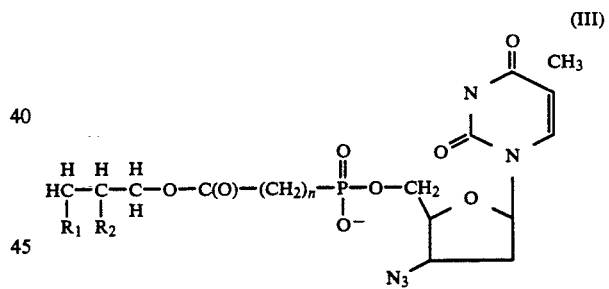

Any nucleoside analogue having anti-viral activity can be used in the above complex. Nucleosides known to have such activity are members of the class comprising 3,-azido-2',3'-dideoxypyrimidine nucleosides, for example, AZT, AZT-P-AZT, AZT-P-ddA, AZT-P-ddI, AzddClU, AzddMeC, AzddMeC N4-OH, AzddMeC N4Me, AZT-P-CyE-ddA, AzddEtU(CS-85), AzddU(CS-87), AzddC(CS-91), AzddFC, AzddBrU, and AzddIU; the class comprising 3'-halopyrimidine dideoxynucleosides, for example, 3-FddClU, 3-FddU, 3-FddT, 3-FddBrU, and 3-FddEtU; the class comprising 2',3'-didehydro-2',3'-dideoxynucleosides (D4 nucleosides), for example, D4T, D4C, D4MeC, and D4A; the class comprising 2',3'-unsubstituted dideoxypyrimidine nucleosides, for example, 5-F-ddC, ddC and ddT; the class comprising 2',3'-unsubstituted dideoxypurines nucleosides, for example, ddA, ddDAPR(diaminopurine), ddG, ddI, and ddMeA(N6 methyl); and the class comprising sugar-substituted dideoxypurine nucleosides, for example, 3-N3ddDAPR, 3-N3ddG, 3-

FddDAPR, 3-FddG, 3-FddaraA, and 3-FddA, wherein Me is methyl, Et is ethyl and CyEt is cyanoethyl.

Other suitable nucleoside analogues may be antiviral agents like acyclovir or gancyclovir (DHPG), or other analogues, as described below. Preferred dideoxy derivatives are those used in the treatment of AIDS, including 3'-azido-3'-deoxythymidine (azidothymidine or AZT); 2',3'-dideoxythymidine (ddT); 2',3'-dideoxycytidine (ddC); 2',3'-dideoxyadenosine (ddA); and 2',3'-dideoxyguanosine (ddG). AZT, ddI, ddA, ddT, and ddC are most preferred analogues at present. The didehydropyrimidines, as well as carbovir, a carbocyclic 2',3'-didehydroguanosine, are also preferred. The 3'-azido derivatives of deoxyguanosine (AZG) and the pyrimidine, deoxyuridine, and the 3'-fluoro derivatives of deoxythymidine and deoxyguanosine are preferred as well. Among the 2',6'-diaminopurines, the 2',3'-deoxyriboside and its 3'-fluoro and 3'-azido derivatives are preferred. Also preferred is 2-chloro-deoxyadenosine.

Among the acyclic sugar derivatives, 9-(4'-hydroxy-1',2'-butadienyl)adenine (adenallene) and its cytosine equivalent are preferred. Preferred acyclic derivatives having a purine or diaminopurine base are 9-(2-phosphonylmethoxyethyl)adenine and phosphonomethoxyethyl deoxydiaminopurine (PMEDADP).

Stereoisomers of these nucleosides, such as 2'-fluoroara-ddA, may be advantageous because of their resistance to acid-catalyzed hydrolysis of the glycosidic bond, which prolongs their antiviral activity. In such cases, they are preferred.

For treating herpes, cytomegalovirus and hepatitis B infections, one may utilize the lipid derivatives of acyclovir, gancyclovir, 1-(2'-deoxy-2'-fluoro-1-β-D-arabinofuranosyl)-5-iodocytosine (FIAC) or 1(2'-deoxy-2'-fluoro-1-β-D-arabinofuranosyl)-5-iodouracil (FIAU).

Liposome Preparation

After synthesis and purification, the lipid derivative of the phosphonoacid, and comprising in some cases an antiviral nucleotide, is incorporated into liposomes, or other suitable carrier. The incorporation can be carried out according to well known liposome preparation procedures, such as sonication and extrusion. Suitable conventional methods of liposome preparation include, but are not limited to, those disclosed by Bangham, et al. (9) Olson, et al. (24), Szoka and Papahadjapoulos (25), Mayhew, et al. (26), Kim, et al. (27), and Mayer, et al. (28).

The liposomes can be made from the lipid derivatives of phosphonoacids alone or in combination with any of the conventional synthetic or natural phospholipid liposome materials including phospholipids from natural sources such as egg, plant or animal sources such as phosphatidylcholine, phosphatidylethanolamine, phosphatidylglycerol, sphingomyelin, phosphatidylserine, or phosphatidylinositol. Synthetic phospholipids that may also be used, include, but are not limited to: dimyristoylphosphatidylcholine, dioleoylphosphatidylcholine, dipalmitoylphosphatidylcholine and distearoylphosphatidycholine, and the corresponding synthetic phosphatidyle thanolamines and phosphatidylglycerols. Other additives such as cholesterol or other sterols, cholesterol hemisuccinate, glycolipids, cerebrosides, fatty acids, gangliosides, sphingolipids, 1,2-bis-(oleoyloxy)-3-(trimethyl ammonio)propane (DOTAP), N-[1-(2,3-dioleoyl) propyl]-N,N,N-trimethylammonium chloride (DOTMA DL-2,3-distearoyloxypropyl(dimethyl)-β-hydroxyethylammonium (29), or psychosine can also be added, as is conventionally known. The relative amounts of phospholipid and additives used in the liposomes may be varied if desired. The preferred ranges are from about 80 to 95 mole percent phospholipid (including the lipid phosphonoacid) and 5 to 20 mole percent psychosine or other additive. Cholesterol, cholesterol hemisuccinate, fatty acids or DOTAP may be used in amounts ranging from 0 to 50 mole percent. The amounts of antiviral phosphonoacids and nucleoside analogue incorporated into the lipid layer of liposomes can be varied with the concentration of their lipids ranging from about 0.01 to about 100 mole percent.

Using conventional methods, approximately 20 to 30% of the phosphonoacid present in solution can be entrapped in liposomes; thus, approximately 70 to 80% of the active compound is wasted. In contrast, where the lipid phosphonoacid is incorporated into liposomes, virtually all of the antiviral compound is incorporated into the liposome, and virtually none of the active compound is wasted.

The liposomes with the above formulations may be made still more specific for their intended targets with the incorporation of monoclonal antibodies or other ligands specific for a target. For example, monoclonal antibodies to the CD4 (T4) receptor may be incorporated into the liposome by linkage to phosphatidylethanolamine (PE) incorporated into the liposome by the method of Leserman, et al. (30).

Therapy of Viral Diseases

The lipid derivatives of the present invention or liposomes comprising these antiviral agents and containing 0.01 to 100% of a lipid derivative such as batyl alcohol phosphonoformic acid or phosphatidylphosphonoformic acid (pPFA) or phosphatidylphosphonoacetate (pPAA) or antiviral analogues of this class of compounds may be administered by parenteral routes to persons infected with HIV. These liposomes can be given to AIDS patients by parenteral administration, enhancing delivery of the compound to macrophages and monocytes, an important reservoir of HIV infection. This will allow for the efficacious use of lower doses of the modified phosphonoacids, reducing toxicity of the compound. These antiviral agents may be used alone or in combination with AZT or other antiretroviral nucleosides of this general class as given conventionally, including but not limited to: ddC, ddA, ddI, ddG, d4T and similar compounds. In addition, it is important to note that liponucleotides of AZT, ddC, ddA, ddI, d4T and ddT as disclosed in a copending application (22) may also be incorporated into the pPFA liposomes singly or in combination to produce ppFA/dideoxynucleoside combination therapies. Alternatively, phosphate esters of the dideoxynucleosides may be encapsulated in the interior of the pPFA liposome as previously described (16) to produce a combination therapy for HIV infections. In addition to using lipid derivatives of phosphonoacids such as pPFA or pPAA in combination with phosphatidylAZT and other liponucleosides incorporated into the same liposome, it is also possible to use lipid derivatives such as those described in II and III above in which the antiviral nucleoside is linked directly to the phosphonoacid.

These combination therapies with AZT and other dideoxyonucleosides are especially important in order to treat more effectively the AZT-resistant (or nucleoside-resistant) strains which have been seen to develop during single drug therapy (31). The use of combination therapy as outlined may greatly reduce the tendency for drug resistant HIV mutant strains to appear and would therefore increase the likelihood of stopping the progression of HIV infection. The same argument would hold equally well in treating herpes infections with regard to the likelihood of developing resistant strains.

The liposome-incorporated phosphorylated nucleoside analogue is administered to patients by any of the known procedures utilized for administering liposomes. The liposomes can be administered intravenously, intraperitoneally, intramuscularly, or subcutaneously as a buffered aqueous solution. Any pharmaceutically acceptable aqueous buffer or other vehicle may be utilized so long as it does not destroy the liposome structure or the activity of the lipid nucleoside analogue. One suitable aqueous buffer is 150 mM NaCl containing 5 mM sodium phosphate with a pH of about 7.4 or other physiological buffered salt solutions.

The dosage for a mammal, including a human, may vary depending upon the extent and severity of the infection and the activity of the administered compound. Dosage levels for the phosphonoacids are well established (2,6,16). Dosage levels of liposomal lipid analogs of phosphonoacids will be about the same as for the phosphonoacid itself, but in general, should be such that about 0.01 mg/kilogram to 1,000 mg/kilogram is administered to the patient on a daily basis and more preferably from about 0.1 mg/kilogram to about 100 mg/kilogram.

The present invention utilizes the antiviral phosphonoformate derivatives noted above incorporated in liposomes in order to direct these compounds to macrophages, monocytes and any other cells which take up the liposomal composition. Ligands may also be incorporated to further focus the specificity of the liposomes. The derivatives described have several unique and novel advantages over the liposomal water soluble phosphonoformates. First, they can be formulated in liposomes to much higher ratios of drug to lipid because they are incorporated into the wall of the liposome instead of being located in the aqueous core compartment. Secondly, the liposomes containing the lipophilio phosphonoformate derivatives noted above do not leak during storage, providing improved product stability. Furthermore, these compositions may be lyophilized, stored dry at room temperature, and reconstituted for use, providing improved shelf life. They also permit efficient incorporation of antiviral compounds into liposomal formulation without significant waste of active compound. A further advantage is that the compositions used in vivo treatment cause a larger percentage of the administered antiviral nucleoside to reach the intended target. At the same time the use of the compositions reduces the amount being taken up by cells in general, thereby decreasing the toxic side effects of the nucleosides. The toxic side effects of the phosphonoformates may be further reduced by targeting the liposomes in which they are contained to actual or potential sites of infection by incorporating ligands into the liposomes.

Lipid derivatives of antiviral agents have a prolonged antiviral effect as compared to the lipid-free agents; therefore they provide therapeutic advantages as medicaments even when not incorporated into liposomes. Non-liposomal lipid derivatives of antiviral phosphonoacids may be applied to the skin or mucosa or into the interior of the body, for example orally, intratracheally or otherwise by the pulmonary route, enterally, rectally, nasally, vaginally, lingually, intravenously, intra-arterially, intramuscularly, intraperitoneally, intradermally, or subcutaneously. The present pharmaceutical preparations can contain the active agent alone, or can contain further pharmaceutically valuable substances. They can further comprise a pharmaceutically acceptable carrier.

Pharmaceutical preparations containing lipid derivatives of antiviral nucleosides are produced by conventional dissolving and lyophilizing processes to contain from approximately 0.1% to 100%, preferably from approximately 1% to 50% of the active ingredient. They can be prepared as ointments, salves, tablets, capsules, powders or sprays, together with effective excipients, vehicles, diluents, fragrances or flavor to make palatable or pleasing to use.

Formulations for oral ingestion are in the form of tablets, capsules, pills, ampoules of powdered active agent, or oily or aqueous suspensions or solutions. Tablets or other non-liquid oral compositions may contain acceptable excipients, known to the art for the manufacture of pharmaceutical compositions, comprising diluents, such as lactose or calcium carbonate; binding agents such as gelatin or starch; and one or more agents selected from the group consisting of sweetening agents, flavoring agents, coloring or preserving agents to provide a palatable preparation. Moreover, such oral preparations may be coated by known techniques to further delay disintegration and absorption in the intestinal tract.

Aqueous suspensions may contain the active ingredient in admixture with pharmacologically acceptable excipients, comprising suspending agents, such as methyl cellulose; and wetting agents, such as lecithin or long-chain fatty alcohols. The said aqueous suspensions may also contain preservatives, coloring agents, flavoring agents and sweetening agents in accordance with industry standards.

Preparations for topical and local application comprise aerosol sprays, lotions, gels and ointments in pharmaceutically appropriate vehicles which may comprise lower aliphatic alcohols, polyglycols such as glycerol, polyethylene glycol, esters of fatty acids, oils and fats, and silicones. The preparations may further comprise antioxidants, such as ascorbic acid or tocopherol, and preservatives, such as p-hydroxybenzoic acid esters.

Parenteral preparations comprise particularly sterile or sterilized products. Injectable compositions may be provided containing the active compound and any of the well known injectable carriers. These may contain salts for regulating the osmotic pressure.

The therapeutically effective amount of the lipid derivatives is determined by reference to the recommended dosages of the active antiviral phosphonoacid, bearing in mind that, in selecting the appropriate dosage in any specific case, consideration must be given to the patient's weight, general health, metabolism, age and other factors which influence response to the drug. The parenteral dosage will be appropriately an order of magnitude lower than the oral dose.

A more complete understanding of the invention can be obtained by referring to the following illustrative examples, which are not intended, however, to unduly limit the invention.

EXAMPLE 1

Synthesis of 1,2-dimyristoyl-glycero-3-phosphonoformate

To a three necked reaction flask was added 0.620 grams of phosphonoformate (PFA; Sigma Chemical Co., St. Louis, Mo.) dissolved in 4 ml of dry pyridine (Aldrich, Milwaukee, Wis.) and 1.28 grams of triisopropylbenzenesulfonyl chloride (Aldrich). 40 ml of 1,2 dimyristoylglycerol (10 mg/ml; Avanti Polar Lipids, Pelham, Ala.) was evaporated and redissolved in 10 ml of freshly distilled dry chloroform and added dropwise to the reaction mixture over a period of 30 minutes. The reaction mixture was stirred overnight at room temperature. After 24 hours, the reaction was stopped by the addition of 50 ml of cold 0.1N HCL. The organic phase was separated, dried over $P_2O_5$ and evaporated under vacuum. The product was crystallized from chloroform and acetone at 20° C. Thin-layer chromatography of the crystallized product, developed in a basic system of chloroform, methanol, ammonia and water (70/30/1/1 by volume) gave three phosphorus-containing products. Further purification of the required compound was obtained by column chromatography. The product, in 50 ml of chloroform, was loaded onto 40 gms of silica gel G, 70–200 mesh, in a glass column measuring 1×14 inches and sequentially eluted with 200 ml of chloroform, 200 ml of chloroform/methanol (1:5), 200 ml of chloroform/methanol (1:10), and finally 300 ml of chloroform/methanol (1:1). Pure 1,2-dimyristoyl-3-phosphonoformate was recovered in the chloroform/methanol (1:1) fraction.

The purity of the compound was checked using two solvent systems, chloroform, methanol, ammonia, and water (70/30/1/1) and chloroform, methanol ammonia and water (65/35/4). The pure compound has an Rf value of 0.54 in the former basic system.

EXAMPLE 2

Synthesis of 1,2-dipalmitoyl-glycero-3-phosphonoformate 1 gram of phosphonoformic acid (PFA), trisodium salt (Fluka, Ronkonkoma, N.Y.) was dissolved in 50 ml of distilled water and passed through a 1.4×10 cm column of Dowex 50-X8 (H+), 200–400 mesh. The PFA-H+ was eluted with water, lyophilized overnight, and dried for 48 hours over $P_2O_5$ in a vacuum oven at room temperature. To a 50 ml round bottom flask containing 15 ml of dry pyridine (Aldrich, Milwaukee, Wis.) was added 120 mg 1,2-dipalmitoylglycerol (Sigma, St. Louis, Mo.) and 230 mg of pFA-H+ and 527 mg of triisopropylbenzenesulfonyl chloride (TPS, Aldrich Milwaukee, Wis.). The vessel was sealed with a rubber serum stopper and flushed with argon. The reaction was stirred overnight under argon and after 24 hours, 15 ml of chloroform/methanol (1:2) was added and the product was precipitated by the addition of 15 ml of acetone at −20° C. The precipitate was collected and recrystallized from chloroform/acetone to obtain 1,2-dipalmitoylglycero-sn-3-phosphonoformate in yield of about 70%.

The product was taken up in a small volume of chloroform/methanol (1:2) and a small aliquot was applied to silica gel G plates (Uniplate, Analtech) and developed with either chloroform/methanol/conc. ammonia/water (70/30/1/1 by volume) or chloroform/methanol/water (65/35/6). The product was present as a phosphoruspositive spot with Rf values of 0.69 or 0.80, respectively. The purity of the compound was estimated to be 70% by visual inspection after charring with concentrated sulfuric acid.

Further purification was achieved by subjecting a portion of the crude product to preparative thin layer chromatography using 20×20 cm plates of silica gel G (silica thickness 0.5 mm, Analtech) developed with chloroform/methanol/conc ammonia/water (70/30/1). The compound was located by spraying reference guide spots on the outside edges of the plate with phosphorus spray, taking care to cover the surface of the remainder of the plate with a clean glass plate. The spot representing the product was scraped and extracted with chloroform/methanol/water (1/2/0.8). The chloroform phase was separated by the addition of chloroform/water (1/1) so that the final ratio of solvents is 1/1/0.9 as described by Bligh and Dyer (32). The chloroform phase was separated and the solvent was evaporated in vacuo and the product was dried by lyophilization from cyclohexane. The purified product gave single spots upon thin layer chromatography in the two systems noted above.

EXAMPLE 3

Liposome Formation With PhosphatidylPFA (pPFA)

To a sterile 2.0 ml sonication vessel were added (in chloroform solution) 7.5 μmols of dioleoylphosphatidyl choline, 4.5 μmols of cholesterol and 3 μmols of pPFA. The solvent was removed in vacuo, forming a thin film of the lipid mixture. The lipid film was hydrated with 0.3 ml of sterile 10 mM sodium acetate buffer (pH 5.0 containing isotonic dextrose. The mixture was vortexed intermittently for 10 minutes followed by sonication for 90 to 120 min using the cup horn of a Heat Systems Ultrasonics sonicator (Model 431B) at output control setting #9, which treatment resulted in clarification of the sample. This sample was diluted with sterile RPMI tissue culture medium and used in HIV experiments at the concentrations indicated.

EXAMPLE 4

Synthesis of Batyl-Phosphonoformate

A quantity of 0.9 grams of racemic batyl alcohol (1-0-hexadecyl-2,3-glycerol, Sigma Chemical, St. Louis, Mo.), 2.6 grams of triisopropylbenzenesulfonyl chloride (TPS, Aldrich, Milwaukee, Wis.) and 0.16 grams of phosphonoformate, acid form, were reacted in 15 ml of dry pyridine at room temperature under nitrogen. The reaction was monitored at half hour intervals by thin layer chromatography as in Example 3 and was judged to be complete at about 24 hours. The reaction was stopped by the addition of 10 ml of chloroform/methanol/Water (1/2/0.8 by volume). The organic (lower) phase was separated by further addition of 2 ml of chloroform and 2 ml of water. The organic phase was removed and evaporated in vacuo and the product was obtained as a white powder. The crude product was dissolved in a small volume of chloroform/methanol (1/1 by volume) and subjected to preparative thin layer chromatography using 0.5 mm layer of silica gel G plates (Analtech, Newark, De.) developed with chloroform/methanol/concentrated ammonia/water (70/30/1/1). Two PFA-containing spots were visualized, scraped and extracted with chloroform/methanol/water as described earlier in Example 3. The two compounds are referred to as batyl-PFA, top and bottom, respectively.

EXAMPLE 5

Demonstration of Anti-HIV Activity in HT4-6C Cells

HT4-6C cells were grown in RPMI 1640 medium containing 100 U/ml penicillin G, 100 ug/ml streptomycin, 2 mM glutamine and 10% fetal bovine serum (Hyclone Laboratories, Logan, Utah). Cells were infected with HIV-1 (LAV-1 strain, L. Montagnier, Paris, France) at a multiplicity of infection sufficient to give 100-300 plaques per well in the no drug controls. Virus was allowed to adsorb at 37° C. for one hour. Liposomes containing the two batyl-PFAs were prepared as described in Example 3. The sonicated preparation was diluted with sterile RPMI buffer and added to the tissue culture wells at the indicated concentrations. After a 3 day incubation at 37° C., the cell monolayers were fixed with 10% formaldehyde and stained with 0.25% crystal violet to visualize plaques. The staining procedure showed individual dense foci of multinucleated giant cells which were counted and used to assess antiretroviral drug activity.

The results of the experiment are shown in FIG. 1. Both preparations of batyl-PFA (top spot and bottom spot) were active in this experiment. The amount of drug required to produce 50% inhibition ($I.C._{50}$) can be estimated from the figure as follows: PFA 200 uM; batylpFA (top) 110 uM and batyl-PFA (bottom) 180 uM.

It should be apparent from the foregoing that other phosphonoacid compounds and lipid derivatives thereof can be substituted in Examples 3 and 5 to obtain similar results. Other antiviral agents, such as, for example, nucleoside analogue phosphates, may also be contained in the aqueous compartments of the liposome (7). The molar percentage of the lipid antiviral agent may vary from 0.1 to 100% of the total lipid mixture. Furthermore, mixtures of antiviral nucleoside lipids may be used in constructing the liposomes for therapy of viral diseases (6). It should be further emphasized that the present invention is not limited to the use of any particular antiviral phosphonoacid; rather, the beneficial results of the present invention flow from the synthesis of the lipid derivatives of these materials and the use of liposomes for formulations for the treatment of viral diseases. Thus, regardless of whether a specific antiviral phosphonoacid is presently known, or whether it becomes known in the future, the methods of forming the presently-contemplated lipid derivatives therefrom are based on established chemical techniques, as will be apparent to those of skill in the art, and their incorporation into liposomes is broadly enabled by the preceding disclosure. It should be emphasized again that the present syntheses are broadly applicable to formation of compounds from essentially all phosphonoacids for use in the practice of the present invention.

Accordingly, the invention may be embodied in other specific forms without departing from it spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced with their scope.

REFERENCES

1. Helgestrand, E. et al. 1978) Science (Washington, D.C.) 201:819.
2. U.S. Pat. No. 4,771,041 to Eriksson et al.
3. Fischl, M. S., Richman, D. D., Grieco, M. H., et al., (1987) New Eng. J. Med., 317: 185-191.
4. Richman, D. D., Fischl, M. A., Grieco, M. H., et al., (1987) New Eng. J. Med., 317: 192-197.
5. Richman, D. D., Kornbluth, R. S. and Carson, D. A. (1987) J. Exp. Med., 166: 11444-1149.
6. Lambert, R. et al.(1989 J. Med. Chem. 32:367-374.
7. Matsushita, T., Ryu, E. K., Hong, C. I. and MacCoss, M. (1981) Cancer Res., 41: 2707-2713.
8. Ho, D. W. H. and Neil, B. L. 1977 Cancer Res., 37: 1640-1643.
9. Bangham, A. D., Standish, M. M. and Watkins, J. C. (1965) J. Mol. Biol., 23: 238-252.
10. Black, C. D. V., Watson, G. J. and Ward, R. J. (1977) Trans. Roy. Soc. Trop. Med. Hyg., 71: 550-552.
11. Alving, C. R., Steck, E. A., Chapman, W. L., Waits, V. B., Hendricks, L. D. Swartz, G. M. and Hanson, W. L. (1978) Proc. Natl. Acad. Sci. U.S.A. 75: 2959-2963.
12. Lopez-Berestein, G. (1986) Ann. Int. Med., 103: 694-699.
13. Herman, E. H., Rahman, A., Ferrans, V. J. Vick, J. A. and Shein, P. S. (1983) Cancer Res., 43: 5427-5432.
14. Ostro, M. (1987) Sci. Am. 256: 103-111.
15. Oberg, B., Pharmacol. Ther. 19:387-415 (1983).
16. Szoka, F. and Chu, C-J., Antimicrobial Agents and Chemotherapy: 32(6) 858-864 (1988).
17. Salahuddin, S. Z., Rose, R. M., Groopman, J. E., Markham, P. D. and Gallo, R. C. (1985) Blood, 68: 281-284.
18. Koenig, S., Gendelman, H. E., Orenstein, J. M. Dalcanto, M. C. Pezeshkpur, G. H., Yungbluth, M. Janotta, F., Aksmit, A., Martin, M. A. and Fauci, A. S. (1986) Science, 233: 1089-1093.
19. Post, G., Kirsch, R. and Koestler, T. (1984) in Liposome Technology, Vol. III, G. Gregoriadis, Ed., CRC Press, Boca Raton, p. 1-28.
20. Scherphof, G. (1986) in Lipids and Biomembranes, Past, Present and Future, op den Kamp, J., Roelofsen, B. and Wirtz, K. W. A., Eds., Elsevier North Holland, Amsterdam, p. 113-136.
21. Hostetler, K. Y., U.S. patent application for LIPID DERIVATIVES OF ANTIVIRAL NUCLEOSIDES FOR LIPOSOMAL INCORPORATION AND METHOD OF USE, Ser. No. 373,088 (1989).
22. Hostetler, K. Y. and D. D. Richman, U.S. patent application for METHOD OF PREPARING ANTIVIRAL DRUGS FOR LIPOSOME ENCAPSULATION FOR THE TREATMENT OF INFECTION WITH THE HUMAN IMMUNODEFICIENCY VIRUS, Ser. No. 099,755 (1987).
23. Agranoff, B. W. and W. D. Suomi, Biochemical Preparations 10:46-51 (1963).
24. Olson, F., Hunt, C. A. Szoka, F. C., Vail, W. J. and Papahadjopoulos, D. (1979) Biochim, Biophys. Acta, 557: 9-23.
25. Szoka, F., and Papahadjopoulos, D. (1978) Proc. Nat. Acad. Sci. 75: 4194-4198.
26. Mayhew, E., Lazo, R., Vail, W. J., King, J., Green, A. M. (1984) 775: 169-175.

27. Kim, S., Turker, M., Chi, E., et al., Biochim. Biophys. Act, 728: 339:348.
28. Mayer, L. D.., Hope, M. J. and Cullis, P. R. (1986) Biochim. Biophys. Acta, 858: 161-168.
29. Rosenthal, A. F. and R. P. Geyer (1960) J. Biol. Chem. 235(8):2202-2206.
30. Leserman, L. D., Barbet, J. and Kourilsky, F. (1980) Nature 288:602-604.
31. Larder, B. A., Darby, G. and Richman, D. D. (1989) Science 243: 1731-1734.
32. Bligh, E. G., and W. J. Dyer Can. J. Biochem., 37: 911, (1959).

What is claimed is:

1. A compound having antiviral activity, comprising:
   a phosphonoacid selected from the group consisting of phosphonoformic acid and phosphonoacetic acid; and
   a lipid selected from the group consisting of sphingolipids, phospholipids, glycerolipids, and fatty acids.

2. The compound of claim 1 wherein said lipid is a 1-O-alkyl-2,3-glycerol.

3. The compound of claim 1 wherein said 1-O-alkyl glycerol is 1-O-hexadecyl-2,3-glycerol.

4. The compound of claim 1 wherein said lipid moiety is a monoacylglycerol or a diacylglycerol.

5. The compound of claim 1 wherein said lipid moiety is a ceramide.

6. The compound of claim 1 wherein said lipid moiety is a cardiolipin.

7. The compound of claim 1 wherein said lipid moiety comprises from 1 to 4 fatty acid moieties, each said moiety comprising from 2 to 24 carbon atoms.

8. A compound according to claim 7, wherein at least one fatty acid moiety of said lipid moiety is unsaturated, and has from 1 to 6 double bonds.

9. A compound according to claim 1, having the formula:

$$(L)_m-(V)_n-W-T$$

wherein
W is

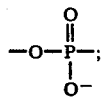

T is $(CH_2)_p-C(O)-O-$;
p = 0 or 1;
L is a lipid selected from the group consisting of sphingolipids, phospholipids, glycerolipids, and fatty acids;
m = 1 to 3;
V is phosphate;
n = 0 to 2 and wherein each L is linked directly to V by a phosphoester bond and T is linked to W by a phosphonate bond.

10. A compound according to claim 1, having the formula:

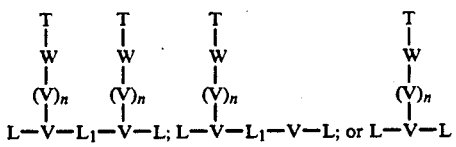

wherein
T is $(CH_2)_p-C(O)-O$;
p is 0 or 1;
V is phosphate;
n is 0 or 1;
W is

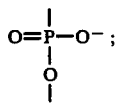

L is a lipid moiety;
L₁ is $(CH_2-CHOH-CH_2)$; and
L and L₁ are linked to V by a phosphoester bond and T is linked to W by a phosphonate bond.

11. A compound according to any one of claims 9 or 10 wherein each L is independently selected from the group consisting of R;

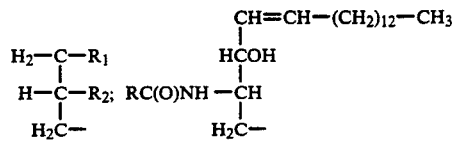

and

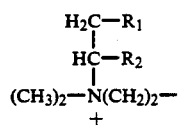

wherein R, R₁ and R₂ are independently C₂ to C₂₄ groups of the formula:

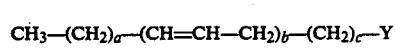

wherein the sum of a and c is from 0 to 22; and b is 0 to 6; and wherein Y is $C(O)O-$, $C-O-$, $C=C-O-$, $C(O)S$, $C-S$, or $C=C-S$.

12. A compound according to claim 11, wherein R₂ is an hydroxyl group.

13. A liposome formed in part from the compound of any one of claims 1 through 12.

* * * * *